United States Patent [19]

Kim

[11] Patent Number: 5,219,870
[45] Date of Patent: Jun. 15, 1993

[54] OMEPRAZOLE COMPOSITIONS DESIGNED FOR ADMINISTRATION IN RECTUM

[76] Inventor: Kwang Sik Kim, 11-43, Yeonmu-dong, Jangan-gu, Suwon, Kyunggi-do, Rep. of Korea

[21] Appl. No.: 661,652

[22] Filed: Feb. 27, 1991

[30] Foreign Application Priority Data

Feb. 27, 1990 [KR] Rep. of Korea .................. 90-2526

[51] Int. Cl.$^5$ .................. A61K 31/44; A61K 31/415; A61K 31/195; A61F 9/02
[52] U.S. Cl. .................................. 514/338; 514/400; 514/564; 514/926; 514/927; 514/966; 514/970; 424/436
[58] Field of Search .............. 514/338, 339, 925, 966, 514/970, 400, 564, 926, 927; 424/436

[56] References Cited

U.S. PATENT DOCUMENTS

| 4,255,431 | 3/1981 | Junggren et al. ................. 514/338 |
| 4,432,966 | 2/1984 | Zeitoun ............................. 424/21 |
| 4,816,568 | 3/1989 | Hamilton, Jr. et al. ........... 530/399 |

FOREIGN PATENT DOCUMENTS 2189698 11/1987 United Kingdom .
2189699 11/1987 United Kingdom .

OTHER PUBLICATIONS

The Merck Index, 11th Ed., #7545. Polyethylene Glycol, 1989.
Rackur, et al., 2-(2-pyridylmethyl)sulfinyl) benzimidazoles; Acid Sensitive Suicide Inhibitors of the Proton Transport System in the Parietal Cell, Apr. 16, 1985, 128 *Biomedical and Biophysical Research Communications*, pp. 477-485.
Pilbrant and Cederberg, Development of an Oral Formulation of Omeprazole; Mar. 1984 International Symposium in Finland, pp. 113-120.

*Primary Examiner*—Jerome D. Goldberg
*Assistant Examiner*—Kimberly Jordan
*Attorney, Agent, or Firm*—Kenyon & Kenyon

[57] ABSTRACT

This invention relates to omeprazole compositions designed for administration in the rectum, wherein said compositions comprise omeprazole, an active ingredient, a mixture of polyethylene glycols having molecular weights 1,000, 1,540, 4,000 and/or 6,000 or a mixture of adeps solidus and sodium laurylsulfate and a soluble, basic amino acid selected from arginine, lysine or histidine.

4 Claims, 1 Drawing Sheet

5,219,870

OMEPRAZOLE COMPOSITIONS DESIGNED FOR ADMINISTRATION IN RECTUM

FIELD OF THE INVENTION

This invention relates to stabilized compositions comprising Omeprazole ("OMP") as an active ingredient, which has been known as an agent having an effect of inhibiting the secretion of gastric acid, and more particularly to a rectal suppository comprising omeprazole, a solubilizing base and a soluble basic amino acid.

BACKGROUND OF THE INVENTION

As an agent having an effect of inhibiting the secretion of gastric acid, OMP is now being used to treat ulcers. However, as OMP itself is quite vulnerable to moisture, temperature, organic solvent, and pH, it is publicly known that its preparation is liable to be easily decomposed and/or transformed.

For example, it is reported that as for the OMP stability in pH, its rapid decomposition occurs in pH less than 4.0; a half life in neutral is about 14 hrs and it is very stable at more than 7.0 (Pilbrant and Cederberg, Scand. J. Gastroenterology, 1985: 20 (Suppl. 108) P113–120.

The acidic decomposition of OMP may be explained by acid-catalyzed rearrangement (G. Rackur et al., Biochem. Biophys. Res. Commun. 1985: 128(1). P477–484). It is reported that with the progress of decomposition, its decomposing rate has been on the drastic increase.

As mentioned in the above, OMP has recognized some disadvantages in that 1) since OMP is easily decomposed by acid or moisture, the manufacture of injectable suspension is not available b) decomposition or transformation is liable to occur under the normal pH of stomach. To cope with this problem, the enteric coated OMP is now being manufactured so as to demonstrate its efficacy in the small intestine, a target area, by maintaining the stabilized condition in oral administration tract.

The present manufacturing process of OMP in a form of enteric coating was suggested in Pilbrant and Cederberg, Scand. J. Gastroenterology, 1985: 20 (Suppl. 108), P113–120. However, it is reported that although said enteric coating has an stability suitable for the study of clinical trials, its long-term stability for storing proves to be reduced.

Also, German Laid-Open patent No. DE-A1-3046559 specified a manufacturing process of OMP in a form of water-soluble endothelial layer coating and secondary enteric coating, but the release of OMP in the small intestine proved not to be effective.

Also, German Laid-Open patent DE-A1-1204363 specified a 3-layer coating process: a) the 1st layer being coated with surface membrane, soluble in gastric juice and insoluble in intestinal juice b) the 2nd layer being coated with water-soluble surface membrane and c) the 3rd layer being an enteric coating. However, the preparation based upon said structure has recognized some disadvantages in that the release of OMP in the small intestine is not rapid and its formulation process is very complicated.

English Patent Applications Nos. 8610572 and 8610573 specified the manufacturing process of stabilized OMP; after adding a stabilizer into OMP to form a core, coating it with water-soluble endothelia layer, and finally, forming the enteric coating.

As far as said method is concerned, the following materials are used for stabilizing: sodium phosphate, citric acid aluminum, mixed aluminum/magnesium oxide, etc. In this method the manufacturing process is very complicated and the desirable stability cannot be obtained.

When OMP preparation is orally administered, it is easily decomposed and transformed under the normal pH of stomach; especially, an enteric coated OMP preparation requires more prolonged time in arriving at the effective serum concentration; an abnormal GI-tract motility may occur and in a concurrent administration with another drug, any exceptional serum concentration may also appear. To prevent the above disadvantages and to demonstrate a rapid absorption efficacy, therefore, a dosage form of OMP through a new administration route is necessary. In an animal experiment using the oral preparation, the possibility on the occurrence of tumor of the stomach is already reported and its long-term intaking might open the pyrolus owing to the enhanced pH in stomach.

To duly cope with the existing disadvantages as above, the inventor has conducted intensive study. With a notion that the pH in the rectum maintains a natural and/or weak alkaline in a range of 7.0, the inventor has succeeded in making said compositions administered to rectum, which may use the absorption of rectal membrane and using by a soluble basic amino acid as stabilizer, said compositions can be stabilized for a prolonged period.

Accordingly, the object of this invention, which differs from the existing ones in an administration route, is to provide stabilized OMp compositions designed for administration in rectum, demonstrating its efficacy through rectum's absorption.

DETAILED DESCRIPTION OF THE INVENTION

Figure 1:
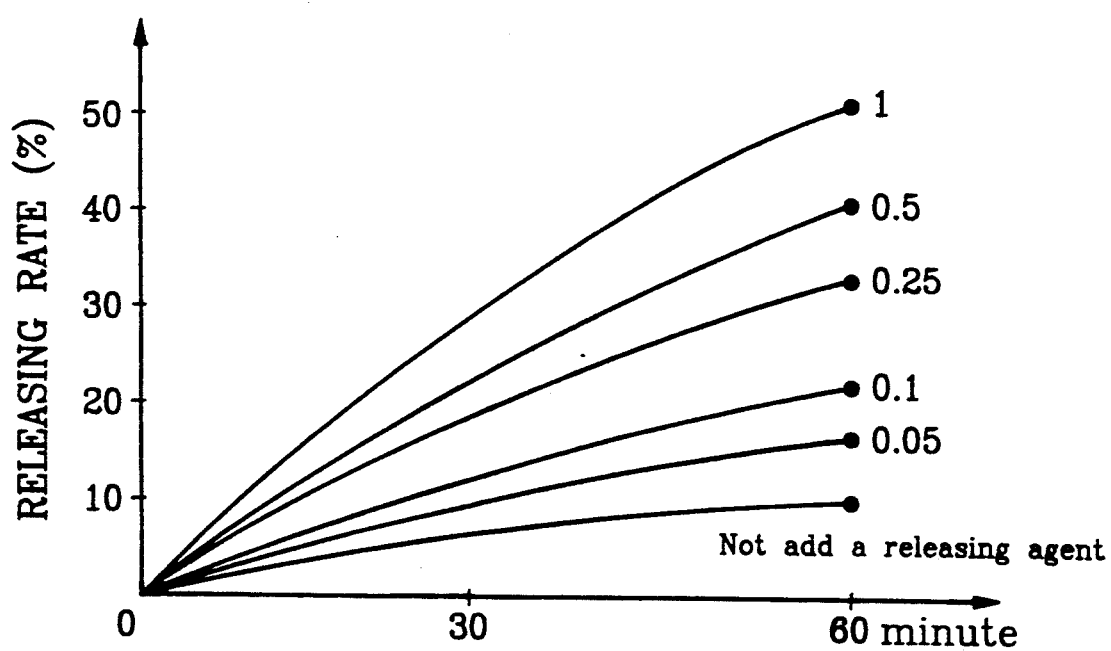
FIG. 1 is a graph showing the releasing rate per hour based upon the amount of releasing agent used in the compositions of this invention.

This invention relates to OMP compositions designed for administration in rectum, wherein said compositions comprise a) OMP, an active ingredient; b) a mixture of polyethylene glycol 1000, 1540, 4,000, 6000 or a mixture of adeps solidus and sodium laurylsulfate; c) any of water-soluble basic amino acid selected from arginine, lysine or histidine.

This invention is further described hereinbelow with reference to a soluble and said compositions, in which:

The manufacture of said compositions provided by this invention is made by using a water-soluble and lipid-soluble base; a mixture of polyethylene glycol (hereinafter referred to as "PEG") 1000, 1540, 4,000, and/or 6000 as water-soluble base and adeps solidus, a mixture of fatty acid and fatty acid ester, as lipid-soluble base. Said bases, after being administered into the rectum, are melted by body fluid or body temperature, and facilitate the absorption of OMP into rectal membrane.

According to this invention of manufacturing said OMP compositions designed for administration in rectum, the use of any stabilizer should be additionally necessary in that a sole mixture of OMP with said bases causes a serious discoloration owing to the decomposition of OMP in its mixing process and storing.

The stabilizer used in this invention includes water-soluble alkali salts, amino acids, etc., but in this invention, any of water-soluble basic amino acids, say, arginine, lysine, or histidine may be preferably used. Said basic amino acids are alkali salts, amino acids, etc., but in this invention, any of water-soluble basic amino acids, say, arginine, lysine, or histidine may be preferably used. Said basic amino acids are used within 0.1–5 mol in proportion to OMP 1 mol, preferably in a mol ratio of 1:1. If the content of said basic amino acids is used in a mol ratio of 1:0.1 in proportion to OMP, the stabilizing effect cannot be expected. Also, if the content is more than 1:5, the absorption effect within small intestine becomes decreased and delayed.

The manufacture of said compositions containing OMP as an active ingredient may be accomplished in the following steps. A mixture of polyethylene glycol 1000, 1540, 4000, 6000 or a mixture of adeps solidus and sodium laurylsulfate, of 90–97 wt % is heated and melted at 70°–80° C., and, thereafter, frozen at 62°–67° C. Thereafter, a 10–3 wt % mixture of OMP and any one of water-soluble basic amino acid selected from arginine, lysine, histidine in a mol ration of 1:0.1–5 mol is admixed, thus filling this into a film, followed by freezing thereof. OMP is preferably used within 1.0–4.0 wt % of total composition.

If adeps solidus is used as a lipid-soluble base, sodium laurylsulfate as a releasing agent may be used within 0.05–1.0 wt % of total compositions' content. Preferrably, adeps solidus is used in 89–97 wt % and for the homogeneous mixture, micro crystalline cellulose may be used as diffusing medium.

Adding releasing agent with the use of lipid-soluble base is preferable because the releasing rate of OMP contained in said lipid-soluble base is quite slow. As described above, this invention relates to the manufacture of stabilized OMP compositions comprising water-soluble (hydrophilic) base, lipid-soluble (lipophilic) base, and stabilizer; in this way, a new type of OMP compositions designed for administration in the rectum may be supplied under the stabilized condition, while solving some problems which the existing inventions has faced.

Said OMP compositions of this invention may heal any GI-tract diseases, when their therapeutically-efficient dose is administered to the host via rectum. And this invention includes such therapeutic method and use as a drug.

The following Examples illustrate some ways in which the principle of this invention has been applied, but are not to be construed as limiting its scope.

REFERENCE 1

OMP Stability Based Upon Kinds of Base

As shown in the following Table 1, PEG 4000 among water-soluble polyethylene glycols was used as a base for the manufacture of said composition; as lipid-soluble adeps solidus, some brandname types such as Witepsol H-15, W-35, S-58 (manufactured by Dynamit Nobel). The manufacture of said compositions were made available by melting and mixing above materials at 75° C. Also, the following Table I shows the stabilities on each item by dividing a) one case of adding 10 mg arginine as a stabilizer and b) the other case not using any stabilizer.

TABLE 1

(unit: mg)

| Classifaction | OMP-Adding | Base-Adding | 7 days | 1 month | 2 months |
|---|---|---|---|---|---|
| NO STABILIZER | | | | | |
| PEG 4000 | 20 | 980 | C | F | black-violet |
| Witepsol W-35 | 20 | 980 | E | very dark black-violet | very dark black-violet |
| Witepsol S-58 | 20 | 980 | D | very dark black-violet | very dark black-violet |
| Witepsol H-15 | 20 | 980 | B | E | pale-violet |
| ARGININE 10 MG ADDING | | | | | |
| PEG 4000 | 20 | 970 | A | A | A |
| Witepsol W-35 | 20 | 970 | B | B | C |
| Witepsol S-58 | 20 | 970 | A | B | C |
| Witepsol H-15 | 20 | 970 | A | A | A |

(Condition: room temperature 20–25° C., single dose 1 g)
Here,
A: nearly unchanged in color.
B: change in color is recognizable but brown is yet to be detected,
C: brown appears apparent and as for other letters, the degree of color is indicated as C < D < E < F.

Results

1) When arginine (stabilizer) was added, stability was more increased than was not).

2) PEG 4000 (water-soluble base) and Witepsol H-15 contributed much to the stabilization.

REFERENCE 2

OMP Stability Based Upon Kinds of Stabilizer

As shown in the following table 2, PEG 4000 and Witepsol H-15 were used as bases for the manufacture of said composition; as a basic amino acid, arginine was used. The stability of said manufactured compositions was observed under a severe condition. As a diffusing medium, micro crystalline cellulose (brandname: Avicel) was used, while using sodium laurylsulfate as a releasing agent.

TABLE 2

| Base | Omeprazole's use | Arginine | NA$_2$HPO$_4$ | Releasing agent | Micro crystaline cellulose | Room temp. 15 days | Room temp. 30 days | 50° C. 7 days | 50° C. 14 day |
|---|---|---|---|---|---|---|---|---|---|
| PEG 4000 | 20 | 10 | — | — | — | A | B | B | C |
| | 20 | 10 | — | 0.5 | — | A | B | B | C |
| | 20 | 10 | — | — | 50 | A | B | B | C |
| | 20 | — | 10 | — | — | C | D | D | E1 |
| | 20 | — | 10 | 0.5 | — | D | B | E | E |
| Witepsol H-15 | 20 | 10 | — | — | — | A | B | F | B |
| | 20 | 10 | — | 0.5 | — | A | B | F | B |
| | 20 | 10 | — | — | 50 | A | B | F | C |
| | 20 | — | 10 | — | — | G | H | E2 | E1 |
| | 20 | — | 10 | 0.5 | — | H | I | E2 | E1 |

(1 g as a single dose)
A: no change in colour
B: same as above
C: discoloration in brown
D: serious discoloration
E1: discoloration into black
E2: black-violet
F: layer-separation is available but with no discoloration
G: pale violet
H: red violet Result As a stabilizer, arginine (water-soluble basic amino acid) has better stabilizing effect than sodium phosphate.

EXAMPLE 1

Compositions Using Water-Soluble Base

The water-soluble base was manufactured by mixing PEG 1540 and PEG 4000 in a ratio of 2:1. Then, at the temperature of 65° C., said OMP compositions were manufactured by mixing 20 mg OMP and any one of stabilizer selected from arginine, lysine, and histidine as shown in the following Table 3.

TABLE 3

| | | No. of Composition | | | | | | | | | (unit: mg) |
|---|---|---|---|---|---|---|---|---|---|---|---|
| | | 1 | 2 | 3 | 4 | 5 | 6 | 7 | 8 | 9 | 10 |
| Active ingredient | OMP | 20 | 20 | 20 | 20 | 20 | 20 | 20 | 20 | 20 | 20 |
| Stabilizer | Arginine | 10 | 20 | 50 | — | — | — | — | — | — | — |
| Stabilizer | Lysine | — | — | — | 8.5 | 20 | 40 | — | — | — | — |
| Stabilizer | Histidine | — | — | — | — | — | — | 9 | 20 | 50 | — |
| Base | Mixture of Polyethylene glycol | 970 | 960 | 930 | 971.5 | 960 | 940 | 971 | 960 | 930 | 980 |

(1 g as a single dose)

Results

When any stabilizer was not used (Compositions No. 10), all materials were entirely decomposed or transformed within 14 days and changed into brown; when any stabilizer was added, their color was unchanged for more than 7 days at 50° C. in 75% of relative humidity.

EXAMPLE 2

Compositions Using Lipid-Soluble Base

By using Witepsol H-15 (lipid-soluble base), said OMP compositions were manufactured in a same manner as did in said Example 1.

TABLE 4

| | | No. of Composition | | | | | | | | | (unit: mg) |
|---|---|---|---|---|---|---|---|---|---|---|---|
| | | 1 | 2 | 3 | 4 | 5 | 6 | 7 | 8 | 9 | 10 |
| Active Ingredient | OMP | 20 | 20 | 20 | 20 | 20 | 20 | 20 | 20 | 20 | 20 |
| Stabilizer | Arginine | 10 | 20 | 50 | — | — | — | — | — | — | — |
| Stabilizer | Lysine | — | — | — | 8.5 | 20 | 40 | — | — | — | — |
| Stabilizer | Histidine | — | — | — | — | — | — | 9 | 20 | 50 | — |
| Base | Witepsol H-15 | 970 | 960 | 930 | 971.5 | 960 | 940 | 971 | 960 | 930 | 980 |

(1 g as a single dose)

Results

When no stabilizer was used (Compositions No. 10), the colors of all materials were entirely changed into brown; when a stabilizer (arginine, lysine, histidine) was added, their color was unchanged for more than 14 days at 50° C. in 75% of humidity.

EXAMPLE 3

Releasing-Rate Modulation of OMP From Lipid-Soluble Base by using sodium laurylsulfate (releasing agent), said OMP compositions were manufactured by the formula of following Table 5 and the releasing rate was measured.

TABLE 5

(unit: mg)

| | | No. of Composition | | | | | |
|---|---|---|---|---|---|---|---|
| | | 1 | 2 | 3 | 4 | 5 | 6 |
| Active Ingredient | OMP | 20 | 20 | 20 | 20 | 20 | 20 |
| Stabilizer | Arginine | 10 | 10 | 10 | 10 | 10 | 10 |
| Releasing Agent | Sodium laurylsulfate | 0.5 | 1 | 2.5 | 5 | 10 | — |
| Base | Witepsol H-15 | 969.5 | 969 | 967.5 | 965 | 960 | 970 |

(1 g as a single dose)

Results

The releasing rate of OMP was increased in line with the amount of sodium laurylsulfate (releasing agent) and the releasing rate per hour based upon the amount of releasing agent was showing in the FIG. 1.

TEST EXAMPLE

Animal Experiment

Manufacture of Compositions Designed for Administration in Rectum

Using the same method as in Reference 1, one composition using water-Soluble base was manufactured by the following formula; 20 mg OMP. 10 mg arginine and 970 mg PEG 4000, and another composition using lipid-soluble base was manufactured by the following formula; 20 mg OMP, 10 mg arginine and 970 mg Witepsol H-15.

Pre Treatment of Experimental Animal

Object: 36 male healthy albino rabbits weighing 1.5–2.3 kg.

Method: before fasting, feed and water were freely provided for eating and rabbits were confined to a wire-box while giving them feed in a constant condition for 4 days. After that, their fasting was made for 48 hours (during the fasting, the rabbits could freely drink 10% dextrose solution.)

I.V. Administration

For comparison test, 4 mg/ml I.V. solution was manufactured in advance by mixing 400 mg OMP, 20 ml polyethylene glycol 4000, and 80 ml buffer solution of 0.1 mol sodium bicarbonate. 5 ml solution per rabbit was administered to its ear's vein.

Oral Administration

As a pre-treatment of test, the experimental rabbits were fasted for 48 hrs with the supply of 10% dextrose solution only. Then, through the esophagus of rabbit, Levine tube in diameter of 5 mm was inserted by 30 cm for administering oral OMP capsules wrapped in paraffin film. To reduce friction, vaseline was applied around the surface of the tube and through a syringe connected to the opposite end of the tube, 30 ml water was injected and, by the water pressure, paraffin film was broken to administer the capsule into intestine.

Rectum Administration

As the feces of the rabbit were not completely removable even in 48-hour fasting, Levine tube having a thickness of 5 mm was used to thrust feces up to the upper part of rectum by 15 cm for the separate of administration of said two kinds of compositions. Then, inserted into the anus, was a cotton wrapped in vinyl tape having a length of 2 cm, fixed it with a clip so as to prevent any leaking of drug solution.

Blood Collection

By using xylene, the venous blood vessel of rabbit's ear was extended to collect some venous blood with a heparinized 3 cc syringe. Said syringe was already treated by soaking its wall with 1000 I.U. heparin. Then, 3 cc of said collected blood sample (10,000 rpm, 10 secs) was centrigued to obtain 1 ml plasma.

Assay

Add 1 ml of said plasma sample to 25 ml intra-standard solution, 3 ml dichloromethane, 3 ml hexaine and 2 ml of 0.1 mol sodium bicarbonate buffer solution. Then, after agitation for 30 secs, centrifuge this mixture in 2000 rpm for 5 mins to separate into organic layer (upper layer) and plasma layer (lower layer).

Put the centrifuged test tube into ice-contained methanol to freeze the plasma layer. Thereafter, take 5 ml organic solvent from the said solution and, under reduced pressure, evaporate the organic solvent by nitrogen gas. Then add 300 μl mobile phase into the residue and after agitation for 30 secs again, centrifuge the mixture in 2000 rpm for 2 mins and conduct the assay by the HPLC analysis (injected 50 μl) through the comparison of height ratio with standard solution.

Test Result

The results of said Test Example were described in the following Table 6, 7, 8, 9: here, Tmax is a time of the peak serum concentration;

Cmax is a peak serum concentration;

AUC is an area under the curve describing serum concentration-time; and

BA is bioavailability.

TABLE 6 unit: μg/ml

I.V. administration
(administration of 20 mg OMP per 2 kg of standard weight)

| | Experiment Animal No. | | | | | | Standard |
|---|---|---|---|---|---|---|---|
| | 1 | 2 | 3 | 4 | 5 | Average | Deviation |
| 1 min | 104.3 | 110.0 | 100.0 | 91.5 | 99.0 | 101.0 | 6.1 |
| 5 min | 45.9 | 47.8 | 63.3 | 58.7 | 56.5 | 54.4 | 6.6 |
| 15 min | 16.4 | 26.4 | 23.8 | 36.8 | 24.5 | 25.6 | 6.6 |

TABLE 6-continued unit: μg/ml

I.V. administration
(administration of 20 mg OMP per 2 kg of standard weight)

|  | Experiment Animal No. | | | | | Average | Standard Deviation |
|---|---|---|---|---|---|---|---|
|  | 1 | 2 | 3 | 4 | 5 | | |
| 30 min | 12.8 | 21.0 | 16.7 | 16.7 | 16.2 | 16.7 | 2.6 |
| 60 min | 7.8 | 9.1 | 9.1 | 11.7 | 6.5 | 8.8 | 1.7 |
| 120 min | 5.8 | 4.6 | 4.2 | 4.4 | 4.4 | 4.7 | 0.2 |
| 180 min | 2.0 | 2.1 | 2.2 | 2.1 | 2.0 | 2.1 | 0.1 |
| AUC | 1989.6 | 2106.5 | 2208.1 | 2190.1 | 2062.8 | — | — |

Average: 2111, standard deviation: 80.96 μg min/ml

TABLE 7 unit: μg/ml

Oral Administration
(Administration of 20 mg OMP per 2 kg of standard weight)

|  | Experiment Animal No. | | | | | Average | Standard Deviation |
|---|---|---|---|---|---|---|---|
|  | 1 | 2 | 3 | 4 | 5 | | |
| 1 hr | 0.293 | 0.300 | 0.492 | 0.270 | 0.295 | 0.330 | 0.082 |
| 2 hr | 0.369 | 0.504 | 0.500 | 0.369 | 0.533 | 0.455 | 0.071 |
| 3 hr | 0.425 | 0.357 | 0.445 | 0.369 | 0.469 | 0.413 | 0.043 |
| 4 hr | 0.591 | 0.410 | 0.375 | 0.531 | 0.376 | 0.477 | 0.078 |
| 5 hr | 0.447 | 0.527 | 0.616 | 0.432 | 0.727 | 0.550 | 0.110 |
| 7 hr | 0.521 | 0.450 | 0.409 | 0.506 | 0.400 | 0.457 | 0.049 |
| 9 hr | 0.341 | 0.360 | 0.373 | 0.356 | 0.365 | 0.357 | 0.010 |
| 11 hr | 0.038 | 0.070 | 0.171 | 0.176 | 0.053 | 0.102 | 0.059 |
| Tmax | 4 hr | 5 hr | 5 hr | 4 hr | 5 hr | — | — |
| Cmax | 0.591 | 0.527 | 0.616 | 0.531 | 0.727 | 0.598 | 0.073 |
| AUC | 364 | 346 | 398 | 356 | 331 | 359 | 22.26 |
| BA | 17.2 | 16.4 | 18.8 | 16.9 | 15.8 | 17 | 1 |

(AUC unit: μg min/ml, Cmax unit: μg/ml, BA unit: %)

TABLE 8 unit: μg/ml

Administration of OMP compositions
in rectum using water-soluble base
(Administration of 20 mg OMP per 2 kg of standard weight)

|  | Experiment Animal No. | | | | | Average | Standard Deviation |
|---|---|---|---|---|---|---|---|
|  | 1 | 2 | 3 | 4 | 5 | | |
| 5 min | 2.81 | 3.29 | 2.11 | 2.05 | 2.66 | 2.58 | 0.461 |
| 15 min | 4.05 | 5.09 | 3.51 | 3.02 | 4.72 | 4.08 | 0.759 |
| 20 min | 3.79 | 5.01 | 5.73 | 6.65 | 5.95 | 5.43 | 0.971 |
| 25 min | 5.40 | 6.48 | 8.89 | 6.69 | 7.41 | 6.97 | 1.150 |
| 40 min | 4.63 | 5.00 | 3.51 | 4.70 | 4.18 | 4.40 | 0.518 |
| 60 min | 3.93 | 4.63 | 3.37 | 3.52 | 4.15 | 3.92 | 0.452 |
| 120 min | 2.31 | 3.03 | 2.11 | 2.51 | 2.16 | 2.42 | 0.333 |
| 180 min | 1.40 | 1.33 | 1.40 | 1.42 | 1.47 | 1.40 | 0.045 |
| Tmax | (25 min) | (25 min) | (25 min) | (25 min) | (25 min) | | |
| Cmax | 5.40 | 6.48 | 8.89 | 6.69 | 7.41 | 6.97 | 1.15 |
| AUC | 767 | 850 | 909 | 877 | 930 | 866.7 | 56.7 |
| BA | 36.3 | 40.3 | 43.1 | 41.5 | 44.0 | 41.0 | 2.69 |

(AUC unit: μg min/ml, Cmax unit: μ/ml, BA unit: %)

TABLE 9 unit: μg/ml

Administration of OMP compositions
in rectum using lipid-soluble base
(Administration of 20 mg OMP per 2 kg of standard weight)

|  | Experiment Animal No. | | | | | Average | Standard Deviation |
|---|---|---|---|---|---|---|---|
|  | 1 | 2 | 3 | 4 | 5 | | |
| 30 min | 2.39 | 3.41 | 2.81 | 1.94 | 2.53 | 2.62 | 0.49 |
| 60 min | 3.66 | 4.30 | 3.58 | 2.41 | 2.69 | 3.32 | 0.69 |
| 90 min | 6.27 | 4.06 | 6.72 | 6.16 | 4.60 | 5.56 | 1.04 |
| 100 min | 3.34 | 3.23 | 2.91 | 3.73 | 3.47 | 3.34 | 0.27 |
| 150 min | 3.41 | 3.07 | 2.84 | 3.58 | 3.21 | 3.22 | 0.26 |
| 210 min | 2.39 | 1.41 | 2.11 | 2.38 | 1.71 | 2.00 | 0.38 |
| 240 min | 1.19 | 0.70 | 1.07 | 1.19 | 0.85 | 1.00 | 0.19 |
| Tmax | 90 min | 90 min | 90 min | 90 min | 80 min | | |
| Cmax | 6.27 | 5.73 | 6.72 | 6.16 | 5.43 | 6.06 | 0.45 |

TABLE 9-continued

Administration of OMP compositions
in rectum using lipid-soluble base
(Administration of 20 mg OMP per 2 kg of standard weight)

unit: μg/ml

| | Experiment Animal No. | | | | | Average | Standard Deviation |
|---|---|---|---|---|---|---|---|
| | 1 | 2 | 3 | 4 | 5 | | |
| AUC | 1193 | 1035 | 1060 | 880 | 949 | 1023 | 106.3 |
| BA | 56.5 | 49.2 | 50.2 | 41.7 | 44.9 | 48.5 | 5.03 |

(AUC unit: μg min/ml, Cmax unit: μg/ml, BA unit: %)

Test Result

The test result shows that:

Oral preparation represented a very low BA of 17%; compositions designed for administration in rectum using water-soluble base was 41% in BA; composition designed for administration in rectum using lipid-soluble base represented a high BA of 49%. From this test result, it is understood that a rectum-administration route has a better body absorption than oral administration. Also, since the compositions designed for administration in the rectum using water-soluble base represented a very low Tmax of 25 mins, there is a possibility for this composition to be selected as a primary dosage form when a prompt absorption is to be required.

Obviously, many modifications and variations of the present invention are possible in light of the above teachings. It is, therefore, to be understood that within the scope of the appended claims, the invention may be practiced otherwise than as specifically described.

What is claimed is:

1. A stabilized rectal suppository containing omeprazole as an active ingredient and amino acid as a stabilizer comprising:

(a) 1.5 to 2.0% by weight omeprazole;

(b) 90 to 97% by weight of a solubilizing base comprising a mixture of adeps solidus and sodium laurylsulfate; and (c) a water soluble, basic amino acid selected from the group consisting of arginine, lysine and histidine, wherein the molar ratio of the amino acid to the omeprazole in the suppository is 0.1 to 5.

2. A process for the manufacture of a stabilized rectal suppository as set forth in claim 1 comprising the steps of: (a) heating and melting a solubilizing base comprising a mixture of adeps solidus and sodium laurylsulfate at a temperature of 70° to 80° C.; (b) cooling said solubilizing base to a temperature in the range of 62°~67° C.; (c) admixing a mixture of omeprazole and a water soluble, basic amino acid selected from the group consisting of arginine, lysine and histidine wherein the molar ratio of the amino acid to the omeprazole in the suppository is 0.1 to 5.0, with said solubilizing base whereby a film is formed; and (d) cooling said admixture from step (c).

3. A method of treating gastric and duodenal ulcer patients wherein said rectal suppository as set forth in claim 1 is administered to the rectum of the patients in a therapeutically-efficient dose.

4. The rectal suppository of claim 1 wherein sodium laurylsulfate is present in the amount of 0.05 to 1.0% by weight.

* * * * *